United States Patent [19]
Lankau et al.

[11] Patent Number: 5,869,481
[45] Date of Patent: Feb. 9, 1999

[54] ANTICONVULSIVE 1-AR(ALK) YLIMIDAZOLIN-2-ONES AND PROCESS FOR MAKING

[75] Inventors: Hans-Joachim Lankau; Manfred Menzer; Klaus Unverferth; Karl Gewald, all of Dresden, Germany; Harry Schäfer, deceased, late of Dresden, Germany, by Helga Ilse Helena Schäfer, Hans Christian Schäfer, Ursel Schäfer, legal representatives

[73] Assignee: Arzneitmittelwerk Dresden G.m.b.H., Germany

[21] Appl. No.: 93,897

[22] Filed: Jun. 9, 1998

Related U.S. Application Data

[63] Continuation-in-part of Ser. No. 708,665, Sep. 4, 1996, abandoned.

[30] Foreign Application Priority Data

Sep. 5, 1995 [DE] Germany ............... 195 32 668.7

[51] Int. Cl.⁶ ............... A61K 31/55; A61K 31/535; A61K 31/495; A61K 31/435; A61K 31/415; C07D 413/04; C07D 403/04; C07D 401/04; C07D 233/66

[52] U.S. Cl. ............... 514/212; 514/235.8; 514/252; 514/326; 514/392; 540/603; 544/139; 544/370; 546/210; 548/321.5

[58] Field of Search ............... 514/212, 235.8, 514/252, 326, 392; 544/370, 139; 546/210; 548/321.5; 540/603

Primary Examiner—Michael G. Ambrose
Attorney, Agent, or Firm—Schweitzer Cornman Gross & Bondell LLP

[57] ABSTRACT

Compounds having anticonsulive activity, of the formula 1

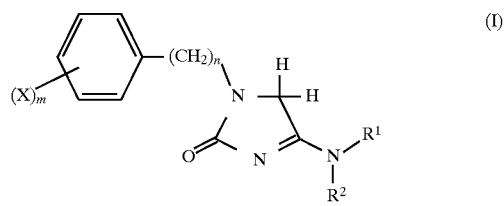

in which X is hydrogen, a $C_{1-4}$-alkyl, $C_{1-4}$ alkoxy, trifluoromethyl, or halogen residue, $R^1$ and $R^2$ are independently of each other $C_{1-4}$-alkyl, $C_{2-4}$ hydroxyalkyl, cycloalkyl or heteroalkyl, or $R^1$ and $R^2$ are together a $C_{2-6}$ alkylene reside in which a —$CH_2$—group is optionally replaced by oxygen, nitrogen or sulfur, m is 0 or 1, and n is 0 or a cardinal number from 1 to 5, and their pharmaceutically acceptable salts. The application also relates to a process for making the compound of formula (I).

7 Claims, No Drawings

ANTICONVULSIVE 1-AR(ALK) YLIMIDAZOLIN-2-ONES AND PROCESS FOR MAKING

This Application is a continuation-in-part of Ser. No. 08/708,665 filed, Sep. 4, 1996 abandoned.

FIELD OF THE INVENTION

The present invention relates to 1-ar(alk)ylimidazolin-2-ones which contain a disubstituted amine radical in the 4-position, processes for their preparation and process for the treatment of disorders of the central nervous systems, in particular of epilepsies of various forms.

BACKGROUND OF THE INVENTION

1-Ar(alk)ylimidazolin-2-ones having an unsubstituted amine or methylamine radical in the 4-position are prepared in the prior art by reaction of ar(alk)ylaminoacetamides with cyanogen bromide. 3-alkyl- or 1-iminoalkyl-3-alkyl-1-ar (alk)ylimidazolin-2-ones are obtained by N-alkylation of the 4-amino-1-ar(alk)ylimidazolin-2-ones prepared in this way, the amino group in the 4-position being tautomerized to an imino group. A further N-alkylation to give compounds of the general formula 1 is therefore not possible, so that compounds according to the invention cannot be prepared by this process [U.S. Pat. No. 4,044,021; DE 2251354].

1-Ar(alk)ylimidazolin-2-ones having a disdubstituted amine radical in the 4-position have not been described until now.

A multiplicity of compounds having anticonvulsive activity are known. However, even today not all epileptic disorders can be treated satisfactorily.

DESCRIPTION OF THE INVENTION

It is an object of the present invention to provide novel compounds with favorable pharmacological properties which can be employed as drugs having an antiepileptic activity.

According to the present invention, these novel compounds are 1-ar(alk)ylimidazolin-2-ones of the formula

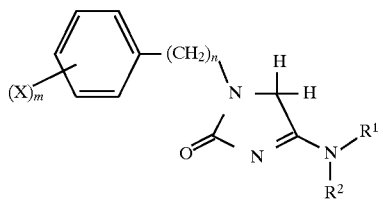

(I)

in which X is hydrogen a $C_{1-4}$-alkyl, $C_{1-4}$ alkoxy, trifluoromethyl, or halogen residue, $R^1$ and $R^2$ are independently of each other a $C_{1-4}$-alkyl, $C_{3-10}$ cycloalkyl or $C_{2-4}$ hydroxyalkyl residue, or $R^1$ and $R^2$ are together a $C_{2-6}$ alkylene residue in which a —$CH_2$— group is optionally replaced by oxygen, nitrogen, or sulfur, n is 0 or 1, and m is 0 or a cardinal number from 1 to 5, and their pharmaceutically acceptable salts.

The number of $CH_2$ groups is either 0 (1-arylimidazolin-2-ones) or 1 (1-aralkylimidazolin-2-ones).

Examples of compounds of the formula (I) include:
1-phenyl-4-morpholinoimidazolin-2-one,
1-(4-methoxy)-4-piperidinoimidazolin-2-one,
1-(4-chlorophenyl)-4-morpholinoimidazolin-2-one,
1-(4-chlorophenyl)-4-piperidinoimidazolin-2-one,
1-(4-chlorophenyl)-4-dimethylaminoimidazolin-2-one,
1-(4-bromopheny)-4-morpholinoimidazolin-2-one,
1-(3-chlorophenyl)-4-morpholinoimidazolin-2-one,
1-(4-chlorophenyl)-4-hexamethyleneiminoimidazolin-2-one,
1-(4-methylphenyl)-4-morpholinoimidazolin-2-one,
1-(4-chlorophenyl)-4-(cyclohexylmethylamino) imidazoline-2-one,
1-(4-fluorophenyl)-4-morpholinoimidazolin-2-one, and
1-benzyl-4-morpholinoimidazolin-2-one.

According to the present invention, the compounds of the formula (I) can be prepared by a novel process by reacting a compound of the formula

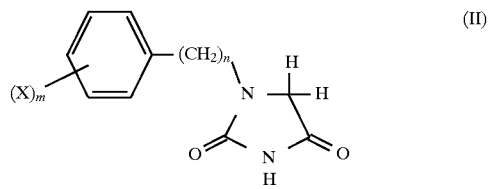

(II)

in which X is hydrogen, a $C_{1-4}$-alkyl, $C_{1-4}$ alkoxy, trifluoromethyl, or halogen residue; n is 0 or 1, and m is 0 or a cardinal number between 1 to 5, with a secondary amine of the formula HNR1R2.

Preparation of the compound of formula (I) can be carried out in a solvent or in excess secondary amine, suitably at temperatures between about 50° C. and about 160° C. Suitable solvents include aromatic hydrocarbons, for example benzene, toluene, chlorobenzene, or dichlorobenzene. The reaction is suitably carried out in the presence of a water-binding substance, such as a zeolite or sodium sulfate. The reaction can be accelerated by conventional condensation catalysts, such as 4-toluenesulfonic acid.

The compounds according to the present invention are suitable for the preparation of anticonvulsive pharmaceutical compositions. Such pharmaceutical compositions can contain as an active ingredient one or more of the compounds of formula (I). Conventional pharmaceutical excipients or auxiliaries can be used to prepare the pharmaceutical compositions.

The medicaments can be administered parenterally (for example intravenously, intramuscularly, or subcutaneously), or orally.

The dosage form for administration can be prepared by processes which are generally known per se and which are customary in pharmaceutical practice.

The compounds according to the invention have strong anticonvulsive actions, and optimum dosages can be determined by residue dosage ranging to determine the optimum anticonvulsively effective dosages.

The compounds of the present invention were tested for their anticonvulsive action in vivo after i.p. administration to mice and p.o. administration to rats according to the internationally customary standard (Pharmac. Weekblad, Sc.Ed. 14, 132 (1992).

The most commonly used chemoconvulsant is pentetrazol which can be used as a primary screen for anticonvulsant activity when dosages that produce hindlimb tonic extension are adminstered. A dose of pentetrazol that produces solely clonic seizures cannot be used as primary screen for new compounds, as phenypyn and carbamazepine have no effect on the blocking of clonic seizures. This test using pentetrazol to induce seizures, used as a primary screen of anticonvulsant activity is referred to in the results below as PEZ.

Seizures can also be reduced electrically for the identification of anticonvulsant activity. This test is referred to below as the MES test for identifying CNS active drugs. A 50 μA (60 HZ) electrical current for 0.2 s is delivered by a corneal electrode to mice. The current is four to five times as large as the threshold current needed to produce the tonic seizure. These specific parameters are used to identify compounds that prevent seizure spread, therapeutic agents for generalized tonic/clonic seizures. Therapeutic agents for absence of seizures are undetected. However, when the current is lower to 12 μA compounds which modify both seizure spread and seizure threshold are identified.

After highly active compounds have been identified by a primary screen, more advance mechanistic and seizure type models are needed to refine the choice for an anticonsulvant. Bicuculline produces seizures by competitively antagonizing the action of GABA. Picrotoxin interacts with chloride ionophore of the GABA/benzodiazepine channel complex.

For example, for the compound 2 (1-(4-chlorophenyl)-4-morpholinoimidazolin-2-one) in the rat the $ED_{50}$ (p.o) for the maximum electroshock was determined to be 21 mg/kg, the $ED_{50}$ in the s.c. pentetrazol test was determined to be 16 mg/kg and the $NT_{50}$ for the neurotoxicity was determined to be >400 mg/kg. In comparison to this, known antiepileptics are active either in the maximum electroshock model or in the pentetrazol test or, in the case of relatively high activity, are severely neurotoxic in the PTX test.

TABLE 1

| Example | Log p octanol/Water part. coeff. | Test | mg/kg | Action in % protected animals |
|---|---|---|---|---|
| 1 | 0.64 | MES | 100 | 30 |
|   |      | PTZ | 100 | 30 |
| 2 | 1.48 | MES | 300 | 30 |
|   |      | PTZ | 30  | 70 |
| 3 | 2.29 | MES | 100 | 100 |
|   |      | PTZ | 100 | 100 |
| 4 | 0.48 | MES | 300 | 30 |
|   |      | PTZ | 300 | 300 |
| 5. | 2.17 | MES | 300 | 100 |
|   |      | PTZ | 300 | 100 |
| 6. | 1.61 | MES | 300 | 100 |
|   |      | PTZ | 100 | 20 |
| 7. | 1.53 | MES | 300 | 100 |
|   |      | PTZ | 100 | 100 |
| 8. | 1.45 | MES | 300 | 30 |
|   |      | PTZ | 100 | 100 |
| 9. | 0.97 | MES | 100 | 30 |
|   |      | PTZ | 100 | 100 |
| 10. | 1.28 | MES | 300 | 30 |
|   |      | PTZ | 300 | 70 |
| 11. | 2.56 | MES | 300 | 100 |
|   |      | PTZ | 300 | 40 |

| Control | Test | Dosage | Action |
|---|---|---|---|
| Carbamazepine | MES | 100 | 100 |
|   | PTZ | 100 | 0 |
| Valproate | MES | 100 | 0 |
|   | PTZ | 100 | 30 |

MES = maximum electroshock
PTZ = s.c. pentetrazole

The compounds of formula (I) were prepared as set out in greater detail in the following examples.

Preparation of the compounds of Formula (I) as specified in Table (2)

EXAMPLES 1–11

Variant A 0.05 mol of 1-arylimidazolin-2,4-dione of formula (II) (n+O) and 200 mg of 4-toluenesulfonic acid were added to 100 ml of an appropriate secondary amine. The mixture is then heated under reflux in a Soxhlet extractor, the extraction thimble being previously filled with about 25 g of a water-binding solid e.g. calcined sodium sulfate, magnesium sulfate, NaOH, KOH, zeolites. After a reaction time of from about 8 to about 30 hours, the solution is filtered hot and distilled to approximately to half the volume in a rotary evaporator. The clear solution is cooled in an ice bath and the crystal magma obtained is separated from the amine. The starting substance contained in the crude product is extracted with 50 ml of hot acetone. The product is recrystallized from n-propanol. About 0.02 mol of unreacted 1-arylimidazolin-2, 4-dione can be recovered from the separated amine.

Variant B 0.05 mol of 1-aralkylimidazolin-2, 4-dione of the formula (II) (n=1) is reacted with a secondary amine as described under Variant A. After a reaction time of from about 8 to about 30 hours, the solution is filtered hot and then concentrated to dryness in a rotary evaporator. 50 ml of methylene chloride and 50 ml of 2N HCl are added to the residue. The organic phase is separated and the aqueous phase is extracted a further two times with methylene chloride. The isolated aqueous phase is rendered alkaline with 50 ml of 10% NaOH and the 1-4 amino-1-aralkylimidazolin-2-one is extracted with 100 m of methylene chloride. The ether extracts are dried over sodium sulfate. After distilling off the methylene chloride, the crude product is recrystallized from ethanol or acetone.

Variant C 0.05 mol of 1-ar(alk)ylimidazolin-2, 4-dione of formula (II) is reacted with 100 ml of dimethylammonium dimethylcarbamate as described under Variants A and B. After a reaction time of 40 hours, the mixture is worked up according to Variant A or B.

TABLE 2

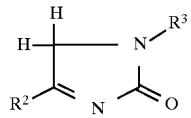

| Example No. | R¹ | R² | Var. | Reaction time (h) | M.p. (°C.) | Yield (%) |
|---|---|---|---|---|---|---|
| 1 | —⟨phenyl⟩ | —N⟨morpholino⟩O | A | 15 | 248 | 42[1)] |
| 2 | —⟨phenyl⟩—Cl | —N⟨morpholino⟩O | A | 15 | 265 | 75[1)] |

TABLE 2-continued (structure at top: R² group with C=N, CH with H,H, and N-R³ connected to C=O in a ring)

| Example No. | R¹ | R² | Var. | Reaction time (h) | M.p. (°C) | Yield (%) |
|---|---|---|---|---|---|---|
| 3 | 4-Cl-C₆H₄ | piperidin-1-yl | A | 20 | 248 | 60[1] |
| 4 | -CH₂-C₆H₅ | morpholin-4-yl | B | 15 | 158 | 48 |
| 5 | 4-Cl-C₆H₄ | 4-methylpiperazin-1-yl | A | 12 | 254 | 68[1] |
| 6 | 4-Cl-C₆H₄ | -N(CH₃)₂ | C | 40 | 292 | 13 |
| 7 | 4-OCH₃-C₆H₄ | piperidin-1-yl | A | 30 | 190 | 52[1] |
| 8 | 4-Cl-C₆H₄ | morpholin-4-yl | A | 15 | 268 | 65[1] |
| 9 | 4-F-C₆H₄ | morpholin-4-yl | A | 18 | 255 | 54[1] |
| 10 | 3-Cl-C₆H₄ | morpholin-4-yl | B | 30 | 237 | 27 |
| 11 | 4-Br-C₆H₄ | piperidin-1-yl | A | 8 | 216 | 88[1] |
| 12 | 4-Cl-C₆H₄ | -N(CH₂-CH₂-OH)₂ | A | 20 | 243 | 23 |

[1] recovered starting material was taken into account when calculating the yield

We claim:
1. Compounds of the formula

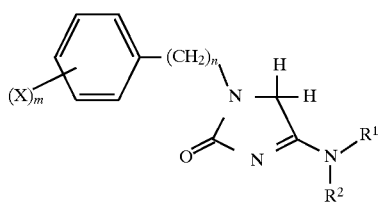

(I)

in which

X is hydrogen, a $C_{1-4}$-alkyl, $C_{1-4}$ alkoxy, trifluoromethyl, or halogen residue, $R^1$ and $R^2$ are independently of each other a $C_{1-4}$-alkyl, $C_{3-10}$ cycloalkyl, or $C_{2-4}$ hydroxyalkyl residue, or $R^1$ and $R^2$ are together are a $C_{2-6}$ alkylene residue in which a —$CH_2$— group is optionally replaced by oxygen, nitrogen, or sulfur, n is 0 or 1, and m is 0 or a cardinal number between 1 and 5, and their pharmaceutically acceptable salts.

2. A compound according to claim 1, the compound being
1-phenyl-4-morpholinoimidazolin-2-one,
1-(4-methoxy)-4-piperidinoimidazolin-2-one,
1-(4-chlorophenyl)-4-morpholinoimidazolin-2-one,
1-(4-chlorophenyl)-4-piperidinoimidazolin-2-one,
1-(4-chlorophenyl)-4-dimethylaminoimidazolin-2-one,
1-(4-bromopheny)-4-morpholinoimidazolin-2-one,
1-(3-chlorophenyl)-4-morpholinoimidazolin-2-one,
1-(4-chlorophenyl)-4-hexamethyleneiminoimidazolin-2-one,
1-(4-chlorophenyl)-4-methylpiperazino) imidazoline-2-one,
1-(4-methylphenyl)-4-morpholinoimidazolin-2-one,
1-(4-chlorophenyl)-4-(cyclohexylmethylamino) imidazoline-2-one,
1-(4-fluorophenyl)-4-morpholinoimidazolin-2-one, and
1-benzyl-4-morpholinoimidazolin-2-one.

3. A process for preparing a compound of claim 1, which comprises contacting a compound of the formula.

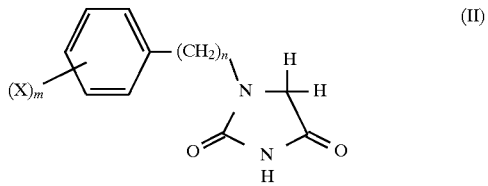

(II)

in which X, $R^1$, $R^2$, n and m have the same definitions as in claim 1, with a secondary amine of the formula $HNR^1R^2$, at a temperature between about 50° C. and about 160° C.

4. A pharmaceutical composition containing as active ingredient at least one compound of claim 1, together with a pharmaceutical excipient, or auxiliary material.

5. A pharmaceutical composition containing as active ingredient at least one compound of claim 2, together with a pharmaceutical excipient or auxiliary material.

6. A process for treating an epileptic disorder in a host, which comprises administering to a host in need therefor an anticonvulsively effective amount of the composition of claim 4.

7. A process for treating an epileptic disorder in a host, which comprises administering to a host in need therefor an anticonvulsively effective amount of the composition of claim 5.

* * * * *